United States Patent
Ridley, Jr. et al.

(10) Patent No.: US 12,264,122 B2
(45) Date of Patent: *Apr. 1, 2025

(54) TAIL GAS UTILIZATION FOR MIXED ALCOHOLS PRODUCTION

(71) Applicant: Standard Alcohol Company of America, Inc., Denver, CO (US)

(72) Inventors: Richard Denham Ridley, Jr., Berthoud, CO (US); Michael Emory Pardun, Denver, CO (US)

(73) Assignee: Standard Alcohol Company of America, Inc., Denver, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/540,167

(22) Filed: Dec. 14, 2023

(65) Prior Publication Data

US 2024/0109825 A1    Apr. 4, 2024

Related U.S. Application Data

(63) Continuation of application No. 17/521,829, filed on Nov. 8, 2021, now Pat. No. 11,845,712.
(Continued)

(51) Int. Cl.
*C07C 29/00* (2006.01)
*B01D 53/00* (2006.01)
(Continued)

(52) U.S. Cl.
CPC .......... *C07C 29/00* (2013.01); *B01D 53/002* (2013.01); *B01D 53/047* (2013.01);
(Continued)

(58) Field of Classification Search
CPC ....... C07C 29/00; C07C 31/04; B01D 53/047; B01D 53/1475; B01D 2252/20489;
(Continued)

(56) References Cited

U.S. PATENT DOCUMENTS

| | | | |
|---|---|---|---|
| 2011/0088896 A1* | 4/2011 | Preston | E21B 43/164 166/266 |
| 2013/0139687 A1* | 6/2013 | Weiss | B01D 53/1493 95/186 |
| 2014/0378560 A1* | 12/2014 | Tijm | C07C 29/157 502/220 |

* cited by examiner

*Primary Examiner* — Jafar F Parsa
(74) *Attorney, Agent, or Firm* — O'Connor & Company; Ryan P. O'Connor

(57) ABSTRACT

It has been discovered that mixed-alcohol production can utilize the waste tail gas stream from the pressure-swing adsorption section of an industrial hydrogen plant. Some variations provide a process for producing mixed alcohols, comprising: obtaining a tail-gas stream from a methane-to-syngas unit (e.g., a steam methane reforming reactor); compressing the tail-gas stream; separating the tail-gas stream into at least a syngas stream, a $CO_2$-rich stream, and a $CH_4$-rich stream; introducing the syngas stream into a mixed-alcohol reactor operated at effective alcohol synthesis conditions in the presence of an alcohol-synthesis catalyst, thereby generating mixed alcohols; and purifying the mixed alcohols to generate a mixed-alcohol product. Other variations provide a process for producing clean syngas, comprising: obtaining a tail-gas stream from a methane-to-syngas unit; compressing the tail-gas stream; separating the tail-gas stream into at least a syngas stream, a $CO_2$-rich stream, and a $CH_4$-rich stream; and recovering a clean syngas product.

16 Claims, 2 Drawing Sheets

Related U.S. Application Data

(60) Provisional application No. 63/112,237, filed on Nov. 11, 2020.

(51) Int. Cl.
  *B01D 53/047* (2006.01)
  *B01D 53/14* (2006.01)
  *B01J 27/04* (2006.01)

(52) U.S. Cl.
  CPC ..... *B01D 53/1475* (2013.01); *B01D 53/1493* (2013.01); *B01J 27/04* (2013.01); *B01D 2252/20405* (2013.01); *B01D 2252/20431* (2013.01); *B01D 2252/20489* (2013.01); *B01D 2253/1122* (2013.01); *B01D 2257/102* (2013.01); *B01D 2257/108* (2013.01); *B01D 2257/304* (2013.01); *B01D 2257/504* (2013.01); *B01D 2257/7025* (2013.01)

(58) Field of Classification Search
  CPC ........ C01B 2203/025; C01B 2203/043; C01B 2203/061; C01B 3/56
  See application file for complete search history.

TAIL GAS UTILIZATION FOR MIXED ALCOHOLS PRODUCTION

PRIORITY DATA

This patent application is a continuation of U.S. patent application Ser. No. 17/521,829, filed on Nov. 8, 2021, which claims priority to U.S. Provisional Patent Application No. 63/112,237, filed on Nov. 11, 2020, each of which is hereby incorporated by reference herein.

FIELD OF THE INVENTION

The present invention generally relates to processes, systems, and apparatus for producing mixed alcohols from syngas, and for integrating mixed-alcohol synthesis with steam methane reforming.

BACKGROUND OF THE INVENTION

Steam reforming or steam methane reforming is a method for producing syngas (hydrogen and carbon monoxide) by reaction of hydrocarbons with water. Commonly natural gas is the feedstock. The main purpose of steam methane reforming is hydrogen production. Steam reforming of natural gas is the largest global source of hydrogen.

The production of hydrogen is very important industrially, since hydrogen is required for many essential chemical processes. Hydrogen is used in the industrial synthesis of ammonia via the Haber process, for example. Other uses of hydrogen include oil refining (e.g., hydrotreating), methanol production, transportation fuels, and hydrogen fuel cells, to name a few.

Conventional steam methane reforming ("SMR") mixes natural gas and steam and uses an external source of hot gas to heat SMR tubes in which a catalytic reaction takes place. The reaction converts steam and lighter hydrocarbons such as methane, commonly using a nickel-based catalyst, to produce a gas stream of carbon monoxide (CO), hydrogen ($H_2$), carbon dioxide ($CO_2$), and small amounts of unconverted methane ($CH_4$) as well as any nitrogen ($N_2$) that entered with the feed gas. The gas stream is referred to as synthesis gas or syngas.

Other methane-to-syngas conversion processes utilize autothermal reforming or partial oxidation. In partial oxidation (POX), a catalyst is utilized to partially oxidize methane with oxygen (pure or in air) to generate syngas. Because it is exothermic, catalytic partial oxidation is less energy-intensive than endothermic steam-methane reforming. Autothermal reforming (ATR) uses oxygen and carbon dioxide or steam in a reaction with methane to form syngas. The reaction usually takes place in a single chamber where the methane is partially oxidized in an exothermic process. The main difference between autothermal reforming and steam-methane reforming is that steam-methane reforming does not require oxygen. Autothermal reforming can be regarded as a hybrid of steam-methane reforming and partial oxidation, in which $H_2/CO$ ratios can be readily varied by adjusting the $H_2O$ and $CO_2$ concentrations in the feed gas. Methane dry reforming is an alternative process for producing syngas by reacting $CH_4$ with $CO_2$ in a highly endothermic catalyzed reaction at high temperatures. This process is not widely used in the gas-processing industries because of rapid catalyst deactivation due to carbon deposition.

The following reactions take place in steam reforming of methane:

$CH_4 + H_2O$ (steam) $\rightarrow CO + 3H_2$ (Endothermic)

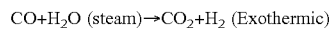

$CO + H_2O$ (steam) $\rightarrow CO_2 + H_2$ (Exothermic)

where the first reaction is the primary reaction of methane with water to form one molecule of CO and three molecules of $H_2$, and the second reaction is the water-gas shift reaction that converts a molecule of CO (from the primary reaction) into $CO_2$ by removing an oxygen atom from water to make more hydrogen. There may be a separate water-gas shift reactor downstream of the steam methane reformer.

Industrial gas companies then pass the syngas through a purification unit to remove the carbon oxides, usually by means of pressure-swing adsorption (PSA) with molecular sieves. The PSA unit works by adsorbing impurities from the syngas stream to leave a pure hydrogen gas. The CO, $CO_2$, and a portion of the $H_2$ are removed from the syngas in pressure-swing adsorption. The gases removed from the syngas are commonly referred to as the tail gas from a PSA unit.

The tail gas stream is typically disposed of as a low-value fuel to feed the SMR burners and provide heat for the reforming reactions. The fuel value of tail gas is approximately 290 BTU per cubic foot, compared to approximately 980 BTU per cubic foot for natural gas. By burning the CO and $H_2$ contained in the tail gas, these valuable gases are wasted, and large volumes of $CO_2$ are emitted to the atmosphere.

Improved processes and systems for hydrogen production, mixed-alcohol synthesis, and methane-to-syngas tail-gas utilization are desired commercially.

SUMMARY OF THE INVENTION

The present invention addresses the aforementioned needs in the art.

Some variations provide a process for producing mixed alcohols, the process comprising:
(a) obtaining a tail-gas stream from a methane-to-syngas unit, wherein the tail-gas stream comprises $CO_2$, CO, $H_2$, and $CH_4$;
(b) compressing the tail-gas stream;
(c) separating the tail-gas stream into at least a syngas stream, a $CO_2$-rich stream, and a $CH_4$-rich stream;
(d) introducing the syngas stream into a mixed-alcohol reactor operated at effective alcohol synthesis conditions and in the presence of an alcohol-synthesis catalyst, thereby generating mixed alcohols and a reactor off-gas; and
(e) optionally purifying the mixed alcohols to generate a mixed-alcohol product.

The methane-to-syngas unit may be a steam reforming reactor, an autothermal reforming reactor, or a partial-oxidation reactor, for example.

In some embodiments, the tail-gas stream is an output of a first pressure-swing adsorption unit.

In some embodiments, the $CO_2$-rich stream is compressed and used in enhanced oil recovery. In these or other embodiments, the $CO_2$-rich stream is sequestered in a geological formation.

In some embodiments, the $CH_4$-rich stream is utilized as a fuel for the methane-to-syngas unit.

In some processes, step (c) further generates a $H_2$-rich stream. This $H_2$-rich stream may be utilized as a fuel for the methane-to-syngas unit. Alternatively, or additionally, the $H_2$-rich stream may be combined with hydrogen produced from the methane-to-syngas unit, to increase the hydrogen production volume.

In some embodiments, step (c) further generates a $N_2$ stream that may be released to the atmosphere.

Step (c) may utilize an amine-based unit, a cryogenic unit, a membrane-separation unit, a second pressure-swing adsorption unit, or a combination thereof. In certain embodiments, step (c) employs a combination of an amine-based unit (referred to also as an amine system) and a cryogenic unit (referred to also as a cold box), in sequential unit operations.

In step (d), the alcohol-synthesis catalyst may be a metal sulfide catalyst, for example.

When step (e) is conducted, this step may include one or more of sulfur removal, dehydration, and distillation, to generate a purified mixed-alcohol stream.

In some embodiments, the reactor off-gas (from the mixed-alcohol reactor) is recycled to step (c). Optionally, the reactor off-gas is treated in a $H_2S$ removal unit prior to recycling to step (c).

The present invention also provides a system for producing mixed alcohols, the system comprising:
a tail-gas compression sub-system configured to receive a tail-gas stream from a methane-to-syngas unit, wherein the tail-gas stream comprises $CO_2$, $CO$, $H_2$, and $CH_4$, and wherein the tail-gas compression sub-system is configured to form a compressed tail-gas stream;
a tail-gas separation sub-system in flow communication with the tail-gas compression sub-system, wherein the tail-gas separation sub-system is configured to separate the compressed tail-gas stream into at least a syngas stream, a $CO_2$-rich stream, and a $CH_4$-rich stream;
a mixed-alcohol reaction sub-system configured to receive at least a portion of the syngas stream, and wherein the mixed-alcohol reaction sub-system is configured to generate mixed alcohols;
optionally, a mixed-alcohol purification sub-system configured to receive the mixed alcohols, and wherein the mixed-alcohol purification sub-system is configured to purify the mixed alcohols to generate purified mixed alcohols; and
a system outlet configured for recovering a mixed-alcohol product.

In some embodiments, the tail-gas separation sub-system is further configured to generate a $H_2$-rich stream.

The tail-gas separation sub-system may include an amine-based unit, a cryogenic unit, a membrane-separation unit, a pressure-swing adsorption unit, or a combination thereof, for example.

The mixed-alcohol reaction sub-system preferably contains a metal sulfide catalyst, or is designed to eventually contain a metal sulfide catalyst when the reactor is under operation to make mixed alcohols.

The mixed-alcohol purification sub-system may contain a sulfur-removal unit, a dehydration unit, a distillation unit, or a combination thereof, for example.

Other variations of the invention provide a process for producing a clean syngas product, the process comprising:
(a) obtaining a tail-gas stream from a methane-to-syngas unit, wherein the tail-gas stream comprises $CO_2$, $CO$, $H_2$, and $CH_4$;
(b) compressing the tail-gas stream;
(c) separating the tail-gas stream into at least a syngas stream, a $CO_2$-rich stream, and a $CH_4$-rich stream; and
(d) recovering the syngas stream as a clean syngas product.

The methane-to-syngas unit may be a steam reforming reactor, an autothermal reforming reactor, or a partial-oxidation reactor, for example.

In some embodiments, the tail-gas stream is an output of a first pressure-swing adsorption unit.

In some embodiments, the $CO_2$-rich stream is compressed and used in enhanced oil recovery. In these or other embodiments, the $CO_2$-rich stream is sequestered in a geological formation.

In some embodiments, the $CH_4$-rich stream is utilized as a fuel for the methane-to-syngas unit.

In some processes, step (c) further generates a $H_2$-rich stream. This $H_2$-rich stream may be recovered and sold. Alternatively, or additionally, this $H_2$-rich stream may be utilized as a fuel for the methane-to-syngas unit. Alternatively, or additionally, the $H_2$-rich stream may be combined with hydrogen produced from the methane-to-syngas unit, to increase the hydrogen production volume.

In some embodiments, step (c) further generates a $N_2$ stream that may be released to the atmosphere.

Step (c) may utilize an amine-based unit, a cryogenic unit, a membrane-separation unit, a second pressure-swing adsorption unit, or a combination thereof. In certain embodiments, step (c) employs a combination of an amine-based unit (referred to also as an amine system) and a cryogenic unit (referred to also as a cold box), in sequential unit operations.

The tail-gas stream obtained from methane-to-syngas unit may be a portion of that unit's overall tail-gas stream, or may be the entirety of that unit's overall tail-gas stream. In some embodiments, a first portion of an overall tail-gas stream is processed according to the processes disclosed herein, while a second portion of the overall tail-gas stream is combusted. Preferably, none of the first portion of tail-gas stream is directly combusted to generate heat. In some embodiments, none of the overall tail-gas stream is directly combusted to generate heat.

Some embodiments further comprise storing and/or selling the clean syngas product.

The process may further comprise converting the clean syngas product to a final product selected from the group consisting of alcohols, aldehydes, olefins, oxygenates, paraffins, linear or branched hydrocarbons, diesel fuel, gasoline, jet fuel, waxes, methane, dimethyl ether, acetic acid, formaldehyde, energy, and combinations thereof, for example. Converting the clean syngas product to a final product may generate a syngas-utilization off-gas. The syngas-utilization off-gas may include unreacted syngas, $CO_2$, $H_2O$, $CH_4$, $N_2$, or other components. Optionally, that syngas-utilization off-gas is recycled to step (c), or a treated form of the syngas-utilization off-gas (e.g., treated to remove $H_2S$) may be recycled to step (c).

Some variations provide a system for producing a clean syngas product, the system comprising:
a tail-gas compression sub-system configured to receive a tail-gas stream from a methane-to-syngas unit, wherein the tail-gas stream comprises $CO_2$, $CO$, $H_2$, and $CH_4$, and wherein the tail-gas compression sub-system is configured to form a compressed tail-gas stream;
a tail-gas separation sub-system in flow communication with the tail-gas compression sub-system, wherein the tail-gas separation sub-system is configured to separate the compressed tail-gas stream into at least a syngas stream, a $CO_2$-rich stream, and a $CH_4$-rich stream; and
a system outlet configured for recovering a clean syngas product.

In some systems, the tail-gas separation sub-system is further configured to generate a $H_2$-rich stream.

The tail-gas separation sub-system may include an amine-based unit, a cryogenic unit, a membrane-separation unit, a pressure-swing adsorption unit, or a combination thereof. In certain embodiments, the tail-gas separation sub-system includes (a) an amine-based unit followed by (b) a cryogenic unit and/or a pressure-swing adsorption unit.

DETAILED DESCRIPTION OF EMBODIMENTS OF THE INVENTION

Figure 1:
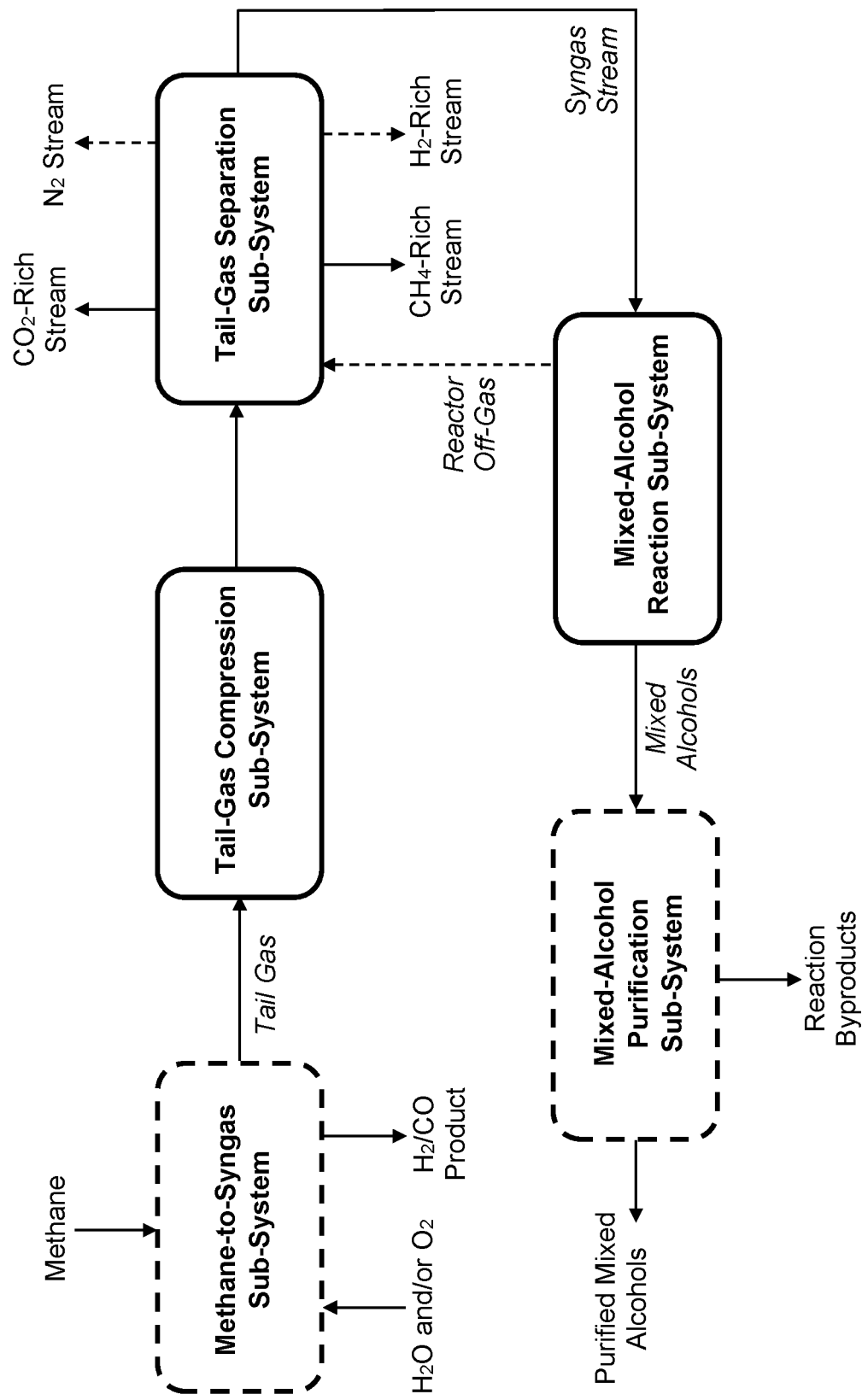
FIG. 1 is an exemplary block-flow diagram according to some embodiments for utilizing methane-production tail gas in mixed-alcohol production.

This description will enable one skilled in the art to make and use the invention, and it describes several embodiments, adaptations, variations, alternatives, and uses of the invention. These and other embodiments, features, and advantages of the present invention will become more apparent to those skilled in the art when taken with reference to the following detailed description of the invention in conjunction with the accompanying drawings.

As used in this specification and the appended claims, the singular forms "a," "an," and "the" include plural referents unless the context clearly indicates otherwise. Unless defined otherwise, all technical and scientific terms used herein have the same meaning as is commonly understood by one of ordinary skill in the art to which this invention belongs.

Unless otherwise indicated, all numbers expressing reaction conditions, stoichiometries, concentrations of components, and so forth used in the specification and claims are to be understood as being modified in all instances by the term "about." Accordingly, unless indicated to the contrary, the numerical parameters set forth in the following specification and attached claims are approximations that may vary depending at least upon a specific analytical technique.

The term "comprising," which is synonymous with "including," "containing," or "characterized by" is inclusive or open-ended and does not exclude additional, unrecited elements or method steps. "Comprising" is a term of art used in claim language which means that the named claim elements are essential, but other claim elements may be added and still form a construct within the scope of the claim.

As used herein, the phrase "consisting of" excludes any element, step, or ingredient not specified in the claim. When the phrase "consists of" (or variations thereof) appears in a clause of the body of a claim, rather than immediately following the preamble, it limits only the element set forth in that clause; other elements are not excluded from the claim as a whole. As used herein, the phrase "consisting essentially of" limits the scope of a claim to the specified elements or method steps, plus those that do not materially affect the basis and novel characteristic(s) of the claimed subject matter.

With respect to the terms "comprising," "consisting of," and "consisting essentially of," where one of these three terms is used herein, the presently disclosed and claimed subject matter may include the use of either of the other two terms. Thus in some embodiments not otherwise explicitly recited, any instance of "comprising" may be replaced by "consisting of" or, alternatively, by "consisting essentially of."

For purposes of an enabling technical disclosure, various explanations, hypotheses, theories, speculations, assumptions, and so on are disclosed. The present invention does not rely on any of these being in fact true. None of the explanations, hypotheses, theories, speculations, or assumptions in this detailed description shall be construed to limit the scope of the invention in any way.

It has been discovered that mixed-alcohol production can utilize the waste tail gas stream from a pressure-swing adsorption section of an industrial hydrogen plant. Variations of the invention provide a process to utilize hydrogen and carbon monoxide, recovered from the tail gas of a methane-to-syngas unit (e.g., a steam-methane reforming reactor), to produce mixed alcohols. It has been further realized that an upgraded tail gas stream from an industrial hydrogen plant may be utilized as syngas for many applications, beyond mixed alcohols.

In some embodiments, a tail gas is compressed and then introduced to a separation sub-system, which may include an amine-based unit, a cryogenic unit, a membrane-separation unit, an additional pressure-swing adsorption unit, or a combination thereof. The outputs of the tail-gas separation sub-system typically include clean syngas ($H_2$ and CO), a $CO_2$ stream, and a $CH_4$-rich stream. A $N_2$ stream may be vented to the atmosphere. The $CO_2$ stream may be utilized for enhanced oil recovery or may be sequestered, for example. In some embodiments, depending on the hydrogen content of the tail gas and the desired $H_2/CO$ ratio in the clean syngas, there is an additional $H_2$ stream that may be sold or used as a fuel, for example.

The clean syngas stream may then be further compressed to a pressure suitable for mixed-alcohol synthesis. The compressed, clean syngas may be introduced to a mixed-alcohol reactor, in which the $H_2$ and CO are heated and passed over an alcohol synthesis catalyst such that at least a portion of the $H_2$ and CO are converted to $C_1$-$C_{10}$ mixed alcohols. Co-products produced in the mixed-alcohol reactor typically include small quantities of water, carbon dioxide, and methane. The mixed alcohols are separated from the gas stream and are further purified, such as sulfur removal, water removal (dehydration), and/or distillation. The separated gas stream may be recycled back to the tail-gas separation unit or first blended with the tail gas stream prior to being fed to the tail-gas separation unit.

Mixed alcohols may be synthesized by passing the cleaned syngas over a potassium-promoted CoS—MoS$_2$ catalyst at about 300° C. and about 100 bar (as merely exemplary conditions for catalysis). See U.S. Pat. Nos. 4,752,622 and 4,882,360, which are hereby incorporated by reference. Processes and catalysts for making mixed alcohols are described in U.S. Pat. Nos. 8,921,431 and 9,290,425, which are hereby incorporated by reference.

The syngas produced as described according to the present invention may be utilized in a number of ways, beyond mixed alcohols. Syngas can be chemically converted into methane, olefins (such as ethylene), oxygenates (such as dimethyl ether), paraffins, linear or branched $C_5$-$C_{15}$ hydrocarbons, diesel fuel, gasoline, or waxes, such as by Fischer-Tropsch chemistry. Syngas can be converted into isobutane by isosynthesis. Syngas can be converted to aldehydes and alcohols by oxosynthesis. Syngas can be converted to methanol as an intermediate for making methanol derivatives including dimethyl ether, acetic acid, ethylene, propylene, or formaldehyde. Syngas can also be converted to energy using energy-conversion devices such as solid-oxide fuel cells, Stirling engines, micro-turbines, internal combustion engines, thermo-electric generators, scroll expanders, gas burners, or thermo-photovoltaic devices.

By employing the processes and systems disclosed herein, the environmental footprint of an existing or new hydrogen production facility may be significantly improved, compared to a hydrogen production facility that does not utilize a disclosed process or system.

Some variations provide a process for producing mixed alcohols, the process comprising:

(a) obtaining a tail-gas stream from a methane-to-syngas unit, wherein the tail-gas stream comprises $CO_2$, CO, $H_2$, and $CH_4$;
(b) compressing the tail-gas stream;
(c) separating the tail-gas stream into at least a syngas stream, a $CO_2$-rich stream, and a $CH_4$-rich stream;
(d) introducing the syngas stream into a mixed-alcohol reactor operated at effective alcohol synthesis conditions and in the presence of an alcohol-synthesis catalyst, thereby generating mixed alcohols and a reactor off-gas; and
(e) optionally purifying the mixed alcohols to generate a mixed-alcohol product.

The methane-to-syngas unit may be a steam reforming reactor, an autothermal reforming reactor, or a partial-oxidation reactor, for example. The methane may be a component of natural gas or may be from another source, a refinery off-gas, a co-product of a chemical plant, etc. The methane may be obtained from a geological formation, such as active or abandoned oil or natural gas fields, a shale play, etc. Alternatively, or additionally, the methane may be obtained from anaerobic digestion of biomass or animal waste, an industrial compost facility, or a landfill.

In some embodiments, the tail-gas stream is an output of a first pressure-swing adsorption unit that is contained within the methane-to-syngas unit, or is downstream of the methane-to-syngas unit. The output of a first pressure-swing adsorption unit may be at a temperature of about 30-50° C. and a pressure of about 1-2 bar, for example.

Step (b) is performed in a tail-gas compression sub-system. The tail-gas compression sub-system is configured to compress the tail-gas stream to a pressure of about 15 bar to about 30 bar, for example, at a temperature from about 30° C. to about 50° C., for example. Compression may be accomplished using a reciprocating compressor, a centrifugal compressor, and/or an axial compressor. Compression may utilize a single compressor or multiple compressors, such as 2, 3, 4, or more individual compressors.

Step (c) is performed in a tail-gas separation sub-system. Step (c) may utilize an amine-based unit, a cryogenic unit, a membrane-separation unit, a second pressure-swing adsorption unit, or a combination thereof. When step (c) utilizes multiple units, those multiple units are all contained within the tail-gas separation sub-system, in series, in parallel, or a combination thereof.

Amine-based units are known for removing $CO_2$ and $H_2S$ from gas streams. In such systems, the amine functions as a solvent to dissolve $CO_2$, which is later removed by adjusting conditions such as temperature.

Cryogenic separation (or cryogenic distillation) may be used for the separation of $CH_4$, $CO_2$, $N_2$, and/or other components, from a syngas stream. Components of the syngas are separated using differences in their boiling points. The syngas may be pretreated to remove any impurities that would freeze at cryogenic temperatures, primarily water and carbon dioxide, and methane at cold enough temperatures.

In certain embodiments, step (c) employs a combination of an amine-based unit (referred to also as an amine system) and a cryogenic unit (referred to also as a cold box), in sequential unit operations to collectively remove $CO_2$, $CH_4$, $N_2$, and optionally $H_2$. It is important, in these embodiments, that the amine system is upstream of the cold box so that high amounts of $CO_2$ do not enter the cold box and potentially cause $CO_2$ freezing and plugging (a problem known as $CO_2$ freeze-out).

Membrane-separation units utilize one or more membranes which enable separation via permeability differences of syngas components. Membranes may be fabricated from polymers, ceramics, and/or zeolites, for example. A multi-stage membrane design may be utilized to separate multiple components, such as $CH_4$, $CO_2$, and $N_2$ out of a $H_2$/CO stream.

Pressure-swing adsorption (PSA) processes are commonly utilized for the production of high-purity hydrogen. Pressure-swing adsorption separates gas species from a mixture of gases under pressure according to differences in species affinities for an adsorbent material. Specific adsorbent materials (e.g., zeolites, activated carbon, silica gel, etc.) are used as a trap, preferentially adsorbing the target gas species at high pressure. The process then swings to low pressure to desorb the adsorbed species. In some embodiments, in step (c), an additional (i.e., separate) pressure-swing adsorption unit is utilized, different than the pressure-swing adsorption unit utilized in the primary methane-to-syngas unit. A PSA unit is preferred when a $H_2$-rich stream is desired from the tail-gas separation sub-system in step (c). Preferably, the pressure-swing adsorption unit (when present) is downstream of both the amine-based unit and the cryogenic unit.

In some embodiments, the $CO_2$-rich stream is compressed and used in enhanced oil recovery. In these or other embodiments, the $CO_2$-rich stream is sequestered in a geological formation. When the $CO_2$-rich stream is geologically sequestered, the environmental footprint is improved because there is a net reduction in greenhouse gas potential due to reduced $CO_2$ in the atmosphere. In some embodiments, the $CO_2$-rich stream is recovered and sold, such as food-grade carbon dioxide or medical-grade dry ice, for example.

In some embodiments, the $CH_4$-rich stream is utilized as a fuel for a boiler or process heater, or combined with a feed gas for conversion. Alternatively, or additionally, the $CH_4$-rich stream may be utilized as a fuel for the methane-to-syngas unit, especially when the methane-to-syngas unit is net-endothermic (e.g., in a steam-reforming reactor).

In some processes, step (c) generates a $H_2$-rich stream. This $H_2$-rich stream may be utilized as a fuel for the methane-to-syngas unit, especially when the methane-to-syngas unit is net-endothermic (e.g., in a steam-reforming reactor). Alternatively, or additionally, the $H_2$-rich stream may be combined with hydrogen produced from the steam methane reforming, to increase the hydrogen production volume.

In some embodiments, step (c) generates a $N_2$ stream that may be released to the atmosphere. In principle, the $N_2$ may be recovered and sold. The $N_2$ may be utilized in the Haber process for ammonia synthesis by reacting the $N_2$ with $H_2$ (e.g., the $H_2$-rich stream) to produce $NH_3$.

In step (d), the alcohol-synthesis catalyst may be a metal sulfide catalyst, for example. The metal sulfide catalyst may be a catalyst comprising crystalline molybdenum sulfide, crystalline cobalt sulfide, and vanadium sulfide. The metal sulfide catalyst may be established in situ in the reactor by sulfiding a metal precursor, disposed within the reactor using a sulfur-containing agent to generate the metal sulfide catalyst.

In step (d), the reactor is pressurized and the syngas is passed over the catalyst. The catalyst and the syngas are heated and mixed alcohols are produced. The mixed-alcohol reaction sub-system may be designed and operated as described in U.S. Pat. No. 9,290,425, for example. The distribution of alcohols may be, for example, 17-31 wt % by weight methanol, 39-49 wt % ethanol, 19-29 wt % propanol, 4-12 wt % butanol, 0.1-5 wt % pentanol, and 0-10 wt % hexanol, heptanol, octanol, nonanol, decanol, ethers, esters, and hydrocarbons (inclusive of all isomers for any of these components).

When step (e) is conducted, this step may include one or more of sulfur removal, dehydration, and distillation, to generate a purified mixed-alcohol stream. See the Example for exemplary desulfurization, dehydration, and distillation to produce a purified mixed-alcohol product.

In some embodiments, the reactor off-gas (from the mixed-alcohol reactor) is recycled to step (c). Optionally, the reactor off-gas is treated in a $H_2S$ removal unit prior to recycling to step (c).

The present invention also provides a system for producing mixed alcohols, the system comprising:
  a tail-gas compression sub-system configured to receive a tail-gas stream from a methane-to-syngas unit, wherein the tail-gas stream comprises $CO_2$, CO, $H_2$, and $CH_4$, and wherein the tail-gas compression sub-system is configured to form a compressed tail-gas stream;
  a tail-gas separation sub-system in flow communication with the tail-gas compression sub-system, wherein the tail-gas separation sub-system is configured to separate the compressed tail-gas stream into at least a syngas stream, a $CO_2$-rich stream, and a $CH_4$-rich stream;
  a mixed-alcohol reaction sub-system configured to receive at least a portion of the syngas stream, and wherein the mixed-alcohol reaction sub-system is configured to generate mixed alcohols;
  optionally, a mixed-alcohol purification sub-system configured to receive the mixed alcohols, and wherein the mixed-alcohol purification sub-system is configured to purify the mixed alcohols to generate purified mixed alcohols; and
  a system outlet configured for recovering a mixed-alcohol product.

In some embodiments, the tail-gas separation sub-system is further configured to generate a $H_2$-rich stream.

The tail-gas separation sub-system may include an amine-based unit, a cryogenic unit, a membrane-separation unit, a pressure-swing adsorption unit, or a combination thereof, for example.

The mixed-alcohol reaction sub-system preferably contains a metal sulfide catalyst, or is designed to eventually contain a metal sulfide catalyst when the reactor is under operation to make mixed alcohols.

The mixed-alcohol purification sub-system may contain a sulfur-removal unit, a dehydration unit, a distillation unit, or a combination thereof, for example.

FIG. 1 depicts an exemplary block-flow diagram of a system and a process, in some embodiments, for producing a mixed-alcohol product. Dotted boxes and lines denote optional units and streams, respectively.

A system is also provided, wherein the system is configured to carry out any of the disclosed processes. For example, a system may be configured to carry out the steps of:
  (a) obtaining a tail-gas stream from a methane-to-syngas unit, wherein the tail-gas stream comprises $CO_2$, CO, $H_2$, and $CH_4$;
  (b) compressing the tail-gas stream;
  (c) separating the tail-gas stream into at least a syngas stream, a $CO_2$-rich stream, and a $CH_4$-rich stream;
  (d) introducing the syngas stream into a mixed-alcohol reactor operated at effective alcohol synthesis conditions and in the presence of an alcohol-synthesis catalyst, thereby generating mixed alcohols and a reactor off-gas; and
  (e) purifying the mixed alcohols to generate a mixed-alcohol product.

Other variations of the invention provide a process for producing a clean syngas product, the process comprising:
  (a) obtaining a tail-gas stream from a methane-to-syngas unit, wherein the tail-gas stream comprises $CO_2$, CO, $H_2$, and $CH_4$;
  (b) compressing the tail-gas stream;
  (c) separating the tail-gas stream into at least a syngas stream, a $CO_2$-rich stream, and a $CH_4$-rich stream; and
  (d) recovering the syngas stream as a clean syngas product.

The methane-to-syngas unit may be a steam reforming reactor, an autothermal reforming reactor, or a partial-oxidation reactor, for example.

In some embodiments, the tail-gas stream is an output of a first pressure-swing adsorption unit.

In some embodiments, the $CO_2$-rich stream is compressed and used in enhanced oil recovery. In these or other embodiments, the $CO_2$-rich stream is sequestered in a geological formation.

In some embodiments, the $CH_4$-rich stream is utilized as a fuel for the methane-to-syngas unit.

In some processes, step (c) further generates a $H_2$-rich stream. This $H_2$-rich stream may be utilized as a fuel for the methane-to-syngas unit. Alternatively, or additionally, the $H_2$-rich stream may be combined with hydrogen produced from the steam methane reforming, to increase the hydrogen production volume.

In some embodiments, step (c) further generates a $N_2$ stream that may be released to the atmosphere.

Step (c) may utilize an amine-based unit, a cryogenic unit, a membrane-separation unit, a second pressure-swing adsorption unit, or a combination thereof. In certain embodiments, step (c) employs a combination of an amine-based unit (referred to also as an amine system) and a cryogenic unit (referred to also as a cold box), in sequential unit operations.

The tail-gas stream obtained from the methane-to-syngas unit may be a portion of that unit's overall tail-gas stream, or may be the entirety of that unit's overall tail-gas stream. In some embodiments, a first portion of an overall tail-gas stream is processed according to the processes disclosed herein, while a second portion of the overall tail-gas stream is combusted. Preferably, none of the first portion of tail-gas stream is directly combusted to generate heat. In some embodiments, none of the overall tail-gas stream is directly combusted to generate heat.

Some embodiments further comprise storing and/or selling the clean syngas product.

The process may further comprise converting the clean syngas product to a final product selected from the group consisting of alcohols, aldehydes, olefins, oxygenates, paraffins, linear or branched hydrocarbons, diesel fuel, gasoline, jet fuel, waxes, methane, dimethyl ether, acetic acid, formaldehyde, energy, and combinations thereof, for example. Converting the clean syngas product to a final product may generate a syngas-utilization off-gas. The syngas-utilization off-gas may include unreacted syngas, $CO_2$, $H_2O$, $CH_4$, $N_2$, or other components. Optionally, that syngas-utilization off-gas is recycled to step (c), or a treated form of the syngas-utilization off-gas (e.g., treated to remove $H_2S$) may be recycled to step (c).

Some variations provide a system for producing a clean syngas product, the system comprising:
- a tail-gas compression sub-system configured to receive a tail-gas stream from a methane-to-syngas unit, wherein the tail-gas stream comprises $CO_2$, CO, $H_2$, and $CH_4$, and wherein the tail-gas compression sub-system is configured to form a compressed tail-gas stream;
- a tail-gas separation sub-system in flow communication with the tail-gas compression sub-system, wherein the tail-gas separation sub-system is configured to separate the compressed tail-gas stream into at least a syngas stream, a $CO_2$-rich stream, and a $CH_4$-rich stream; and
- a system outlet configured for recovering a clean syngas product.

In some systems, the tail-gas separation sub-system is further configured to generate a $H_2$-rich stream.

The tail-gas separation sub-system may include an amine-based unit, a cryogenic unit, a membrane-separation unit, a pressure-swing adsorption unit, or a combination thereof. In certain embodiments, the tail-gas separation sub-system includes (a) an amine-based unit followed by (b) a cryogenic unit and/or a pressure-swing adsorption unit.

Figure 2:
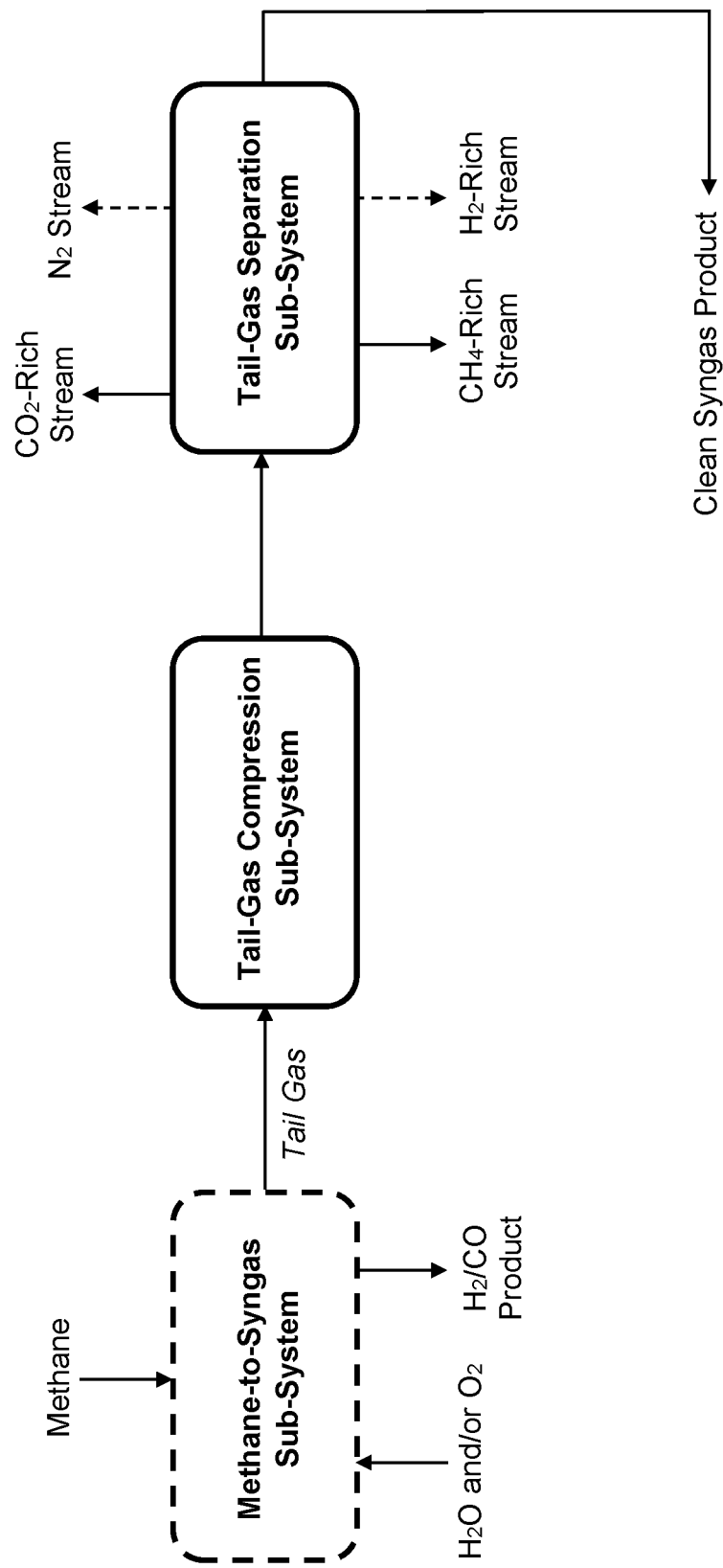
FIG. 2 is an exemplary block-flow diagram according to some embodiments for utilizing methane-production tail gas in syngas production.

FIG. 2 depicts an exemplary block-flow diagram of a system and a process, in some embodiments, for producing a clean syngas product. Dotted boxes and lines denote optional units and streams, respectively.

Other embodiments provide a system configured to carry out the steps of:
- (a) obtaining a tail-gas stream from a methane-to-syngas unit, wherein the tail-gas stream comprises $CO_2$, CO, $H_2$, and $CH_4$;
- (b) compressing the tail-gas stream;
- (c) separating the tail-gas stream into at least a syngas stream, a $CO_2$-rich stream, and a $CH_4$-rich stream; and
- (d) recovering the syngas stream as a clean syngas product.

The process is preferably conducted continuously or semi-continuously. There may be various recycle schemes in the process, including during steady-state operation, start-up or shut-down.

As will be appreciated by a skilled engineer, the processes and systems of the invention may employ various process sensors and control schemes to monitor and control gas pressures, temperatures, flow rates, and compositions throughout processing. Standard or customized gas pressure, temperature, and flow gauges may be employed. Gas composition may be monitored by withdrawing a gas sample and subjecting the gas sample to mass spectrometry, gas chromatography, or FTIR spectroscopy, for example. Gas composition may be measured, for example, according to ASTM D7833, D1945, D1946, or D3588, which test methods are incorporated by reference herein. Process adjustments may be made dynamically using measurements of gas pressures, temperatures, flow rates, and/or compositions, if deemed necessary or desirable, using well-known principles of process control (feedback, feedforward, proportional-integral-derivative logic, etc.).

As will also be appreciated by a skilled artisan, the processes and systems of the invention may utilize various process simulations, modeling, and engineering calculations, both in the initial design as well as during operation. Process calculations and simulations may be performed using process simulation software.

The present invention may be applied to a wide range of throughputs and product generation capacities, such as from about 1,000 liters/day to about 1,000,000 liters/day of mixed alcohols, or from about 10 MMSCFD to about 10,000 MMSCFD of a clean syngas product, for example.

In addition to the mixed alcohols or clean syngas as primary product, there may be a number of co-products from the processes and systems of the invention. Co-products may include, but are not limited to, $CH_4$, $H_2$, CO, $CO_2$, $N_2$, $H_2O$, hydrocarbons, and electricity generated on-site, for example.

Also provided is a mixed-alcohol composition produced by any of the disclosed processes. The mixed-alcohol composition may be as described in U.S. Pat. No. 8,921,431 or U.S. Pat. No. 9,290,425, or another composition.

For example, some embodiments provide a mixed-alcohol product produced by a process comprising:
- (a) obtaining a tail-gas stream from a methane-to-syngas unit, wherein the tail-gas stream comprises $CO_2$, CO, $H_2$, and $CH_4$;
- (b) compressing the tail-gas stream;
- (c) separating the tail-gas stream into at least a syngas stream, a $CO_2$-rich stream, and a $CH_4$-rich stream;
- (d) introducing the syngas stream into a mixed-alcohol reactor operated at effective alcohol synthesis conditions and in the presence of an alcohol-synthesis catalyst, thereby generating mixed alcohols and a reactor off-gas; and
- (e) purifying the mixed alcohols to generate a mixed-alcohol product.

Other embodiments provide a syngas product produced by a process comprising:
- (a) obtaining a tail-gas stream from a methane-to-syngas unit, wherein the tail-gas stream comprises $CO_2$, CO, $H_2$, and $CH_4$;
- (b) compressing the tail-gas stream;
- (c) separating the tail-gas stream into at least a syngas stream, a $CO_2$-rich stream, and a $CH_4$-rich stream; and
- (d) recovering the syngas stream as a clean syngas product.

Other embodiments provide a product produced by a process comprising:
- (a) obtaining a tail-gas stream from a methane-to-syngas unit, wherein the tail-gas stream comprises $CO_2$, CO, $H_2$, and $CH_4$;
- (b) compressing the tail-gas stream;
- (c) separating the tail-gas stream into at least a syngas stream, a $CO_2$-rich stream, and a $CH_4$-rich stream; and
- (d) converting the syngas stream to a product, which is optionally selected from the group consisting of alcohols, aldehydes, olefins, oxygenates, paraffins, linear or branched hydrocarbons, diesel fuel, gasoline, jet fuel, waxes, methane, dimethyl ether, acetic acid, formaldehyde, energy, and combinations thereof.

EXAMPLE

This example illustrates tail-gas utilization for mixed alcohol production, according to the principles of the invention described above. The flow rates and concentrations in this Example are merely exemplary and not intended to limit the invention as claimed.

This example is a process simulation carried out using Aspen Plus® software (Aspen Technology Inc., Bedford, Massachusetts, USA). Using Aspen Plus, a process model is built and then the process is simulated using complex calculations involving unit operations, chemical reactions, thermodynamic properties, and so on, to predict performance of the designed process.

A tail-gas stream is obtained from a steam methane reforming system that produces 200 million standard cubic feet per day (MMSCFD) of high-purity hydrogen (200 MMSCFD is about 65.6 standard m³/s). The steam methane reforming system is configured with a water-gas shift reactor to react steam with CO, forming $H_2$ and $CO_2$. The steam methane reforming system is also configured with a pressure-swing adsorption unit to separate the high-purity hydrogen as the primary product, at 200 MMSCFD $H_2$. A steam methane reforming system is a type of methane-to-syngas sub-system as shown in FIG. 1.

The tail-gas stream from the steam methane reforming system has a flow rate of 121.9 MMSCFD and has the following composition on a volumetric basis: 10.0 vol % CO, 46.4 vol % $CO_2$, 24.2 vol % $H_2$, 17.8 vol % $CH_4$, 0.9 vol % $H_2O$, and 0.6 vol % $N_2$. The tail-gas stream is at a temperature of about 38° C. and atmospheric pressure. Note that in the process simulation, there are minor amounts of $C_{2+}$ hydrocarbons (such as ethane) that track with the methane and will not be reported in this example.

The tail-gas stream is compressed using a tail-gas compressor to a pressure of about 30 bar. The temperature of the compressed tail gas is about 50° C.

The compressed tail gas is then fed to a tail-gas separation sub-system. The tail-gas separation sub-system is configured with an amine system followed by a cryogenic separation unit, operated in sequence.

The feed stream to the amine system has a flow rate of 177.9 MMSCFD and has the following composition: 20.6 vol % CO, 34.3 vol % $CO_2$, 30.7 vol % $H_2$, 13.4 vol % $CH_4$, 0.3 vol % $H_2O$, and 0.6 vol % $N_2$. In this Example, the feed stream to the amine system is a combination of the compressed tail gas and recycled reactor off-gas described below.

The amine system is a conventional amine-separation unit. The specific amine solvent employed is methyl diethanolamine (MDEA). In an absorber column, $CO_2$ is absorbed into the MDEA to form a soluble carbonate salt. The absorber operates at 50° C. and 30 bar pressure. In a stripping column, the $CO_2$ is released by heating the carbonate salt at 90° C. and a pressure of about 1.5 bar.

The purified gas (also referred to as sweet gas) from the amine system has a flow rate of 117.8 MMSCFD and a composition as follows: 31.2 vol % CO, 1.0 vol % $CO_2$, 46.3 vol % $H_2$, 20.2 vol % $CH_4$, 0.3 vol % $H_2O$, and 1.0 vol % $N_2$. The purified gas is fed to the cryogenic separation unit described below.

The flow rate of the $CO_2$ produced by the amine system is 60.7 MMSCFD of high-purity $CO_2$, nominally at a concentration of 100 vol %. This high-purity $CO_2$ may be used for enhanced oil recovery or may be sequestered to remove the $CO_2$ from the atmosphere (or avoid emission of $CO_2$). The $CO_2$ may be compressed to a suitable pressure for enhanced oil recovery or sequestration, such as about 50-100 bar. The high-purity $CO_2$ may be further purified and sold for applications that require relatively high $CO_2$ purity, such as to the food/beverage industry or use as medical-grade dry ice, for example.

The tail-gas separation sub-system also includes a cryogenic separation unit to separate out $CH_4$ and optionally $N_2$ from syngas. The feed to the cryogenic separation unit is 117.8 MMSCFD with composition described above. The cryogenic separation unit is operated at a cold-box temperature of about −173° C. and a cold-box pressure of about 50 bar. At a pressure of 50 bar, methane can be separated at approximately −100° C., and nitrogen can be separated at approximately −150° C.

A clean syngas stream is produced by the cryogenic separation unit at a flow rate of 91.1 MMSCFD, containing 38.9 vol % CO and 61.1 vol % $H_2$, with a $H_2$/CO molar ratio of 1.57.

In this example, the $N_2$ from the cryogenic separation unit is at a flow rate of only 0.66 MMSCFD and is not recovered; the $N_2$ goes with the fuel gas stream described below. Optionally, the nitrogen stream may be vented to the atmosphere, noting that $N_2$ is not a greenhouse gas and is the majority of ordinary air.

Another output of the cryogenic separation unit is a fuel gas stream at a flow rate of 26.1 MMCSFD, containing 87.2 vol % $CH_4$ and 5.7 vol % CO, 4.6 vol % $H_2$, and 2.5 vol % $N_2$. The fuel gas stream has a high energy value when combusted. The heat of combustion may be utilized to drive the endothermic steam reforming in the steam methane reforming system. Optionally, because the fuel gas stream is mostly methane, this stream may be recycled to feed the steam methane reforming system.

Another output of the cryogenic separation unit is a hydrogen stream at a flow rate of 19.7 MMSCFD, consisting essentially of $H_2$. The hydrogen stream may be sold, such as to an adjacent refinery for on-site hydrogen requirements or may be combined with the high-purity hydrogen product produced by the steam methane reforming system, adding 9.9% to the site product output, for instance. The hydrogen may be utilized in the steam methane reformer burners to displace natural gas or other fuels needing to be burned to generate the necessary energy for endothermic steam reforming. In other scenarios in which a different $H_2$/CO ratio is desired for the clean syngas, there may or may not be excess hydrogen available.

The clean syngas stream produced by the cryogenic separation unit has a flow rate of 71.4 MMSCFD and is 50 vol % CO and 50 vol % $H_2$. This clean syngas stream is fed to a syngas compressor, to raise the syngas pressure to about 100 bar. The compressed syngas is also preheated to a temperature of about 300° C. The compressed, preheated syngas is fed to a mixed-alcohol reactor.

The mixed-alcohol reactor is a fixed-bed continuous reactor containing a potassium-promoted and sulfided CoS—$MoS_2$ catalyst. The mixed-alcohol reactor is designed and operated according to commonly owned U.S. Pat. No. 9,290,425, which has been incorporated by reference. In the mixed-alcohol reactor, syngas is converted to methanol, ethanol, propanol, butanol, pentanol, and small amounts of higher alcohols.

The syngas conversion to mixed alcohols in the mixed-alcohol reactor is about 30%. The consumed syngas is 13.7 MMSCFD (6.5 MMSCFD CO and 6.7 MMSCFD $H_2$). The flow rate of the reactor off-gas is 56.5 MMSCFD, and its composition is 43.5 vol % CO, 7.6 vol % $CO_2$, 44.3 vol % $H_2$, 3.9 vol % $CH_4$, 0.01 vol % $H_2O$, and 0.8 vol % $N_2$.

Following mixed-alcohol synthesis, a mixed-alcohol stream is generated, as well as a reactor off-gas. The reactor off-gas is let-down in pressure and is fed to a H$_2$S removal unit. The H$_2$S removal unit utilizes adsorbent media, such as an iron-based scavenger, to selectively adsorb H$_2$S. Following H$_2$S removal, the off-gas is recycled to the amine system as noted earlier. If the reactor off-gas does not contain much H$_2$S, the H$_2$S removal unit may be omitted. The reactor off-gas may also be purged from the process and not internally recycled.

The raw mixed-alcohol stream is fed to a sulfur-removal unit. The sulfur-removal unit includes a sulfur absorbent such as an ion-exchange resin, activated carbon, alumina, aluminum silicate, or a combination thereof, to absorb or adsorb sulfur-containing compounds from the raw mixed-alcohol stream, forming a low-sulfur mixed-alcohol stream. The sulfur absorbent is regenerable using a heated, inert stripping gas for regenerating the sulfur absorbent beds. The stripping gas may be nitrogen, optionally including N$_2$ recycled from the cryogenic separation unit, and may be heated using electrical heating, for example. If the raw mixed-alcohol stream does not contain much sulfur, the sulfur-removal unit may be omitted.

The low-sulfur mixed-alcohol stream is fed to a dehydrator to remove water from the mixed alcohols. The dehydrator contains zeolite-based molecular-sieve membranes for water adsorption. Dehydration occurs prior to distillation.

The dehydrated, low-sulfur mixed-alcohol stream is fed to a distillation column to remove a majority of the impurities (primarily methanol), resulting in a mixed-alcohol product. This simulated process produces 146,586 liters per day of high-value and environmentally friendly mixed alcohols. The mixed-alcohol product may be referred to as OctaneX® mixed alcohols.

The clean syngas stream produced by the cryogenic separation unit alternatively may be recovered and sold, rather than being converted to mixed alcohols. The clean syngas stream may ultimately be converted to a wide variety of final products.

In the simulated process, approximately 22,700 kg/hr of high-pressure steam is generating using excess heat from the mixed-alcohol reactor. The high-pressure steam is sent to a cogeneration unit in which the steam is superheated and then used in a turbine to generate electricity. 0.5 MW/hr of power is generated for the entire process including process pumps, a vacuum pump used in the dehydration unit, and the heater used in the sulfur removal unit.

In this detailed description, reference has been made to multiple embodiments of the invention and non-limiting examples relating to how the invention can be understood and practiced. Other embodiments that do not provide all of the features and advantages set forth herein may be utilized, without departing from the spirit and scope of the present invention. This invention incorporates routine experimentation and optimization of the methods and systems described herein. Such modifications and variations are considered to be within the scope of the invention defined by the claims.

All publications, patents, and patent applications cited in this specification are herein incorporated by reference in their entirety as if each publication, patent, or patent application were specifically and individually put forth herein.

Where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially.

Therefore, to the extent there are variations of the invention, which are within the spirit of the disclosure or equivalent to the inventions found in the appended claims, it is the intent that this patent will cover those variations as well. The present invention shall only be limited by what is claimed.

What is claimed is:

1. A process for producing and using a clean syngas product, said process comprising:
    (a) obtaining a tail-gas stream from a methane-to-syngas unit, wherein said tail-gas stream comprises CO$_2$, CO, H$_2$, and CH$_4$;
    (b) compressing said tail-gas stream;
    (c) separating said tail-gas stream into at least a syngas stream, a CO$_2$-rich stream, and a CH$_4$-rich stream;
    (d) recovering said syngas stream as a clean syngas product;
    (e) converting said clean syngas product to a final product selected from the group consisting of alcohols, aldehydes, olefins, oxygenates, paraffins, linear or branched hydrocarbons, diesel fuel, gasoline, jet fuel, waxes, methane, dimethyl ether, acetic acid, formaldehyde, energy, and combinations thereof, wherein a syngas-utilization off-gas is generated in connection with said converting said clean syngas product to said final product; and
    (f) recycling said syngas-utilization off-gas, or a treated form thereof, to step (c).

2. The process of claim 1, wherein said methane-to-syngas unit is a steam reforming reactor, an autothermal reforming reactor, or a partial-oxidation reactor.

3. The process of claim 1, wherein said tail-gas stream is an output of a first pressure-swing adsorption unit.

4. The process of claim 1, wherein said CO$_2$-rich stream is compressed and used in enhanced oil recovery.

5. The process of claim 1, wherein said CO$_2$-rich stream is sequestered in a geological formation.

6. The process of claim 1, wherein said CH$_4$-rich stream is utilized as a fuel for heating said methane-to-syngas unit.

7. The process of claim 1, wherein step (c) further generates a H$_2$-rich stream.

8. The process of claim 7, wherein said H$_2$-rich stream is recovered.

9. The process of claim 8, wherein said H$_2$-rich stream is combined with hydrogen produced from said methane-to-syngas unit.

10. The process of claim 8, wherein said H$_2$-rich stream is utilized as a fuel for heating said methane-to-syngas unit.

11. The process of claim 8, wherein said H$_2$-rich stream is combined with hydrogen produced from said methane-to-syngas unit, to increase hydrogen production volume.

12. The process of claim 1, wherein step (c) further generates a N$_2$ stream that is released to the atmosphere.

13. The process of claim 1, wherein step (c) utilizes an amine-based system, a cryogenic system, a membrane-separation system, a second pressure-swing adsorption unit, or a combination thereof.

14. The process of claim 1, wherein step (c) employs a combination of an amine-based unit and a cryogenic unit, in sequential unit operations.

15. The process of claim 1, wherein none of said tail-gas stream is directly combusted to generate heat.

16. The process of claim 1, wherein syngas-utilization off-gas is treated to remove H$_2$S prior to recycling to step (c).

* * * * *